US012402976B2

(12) United States Patent
Lomes et al.

(10) Patent No.: US 12,402,976 B2
(45) Date of Patent: Sep. 2, 2025

(54) AUGMENTED REALITY SOFT TISSUE BIOPSY AND SURGERY SYSTEM

(71) Applicant: SPRINGLOC LTD, Hosen (IL)

(72) Inventors: Alexander Lomes, Moshav Hosen (IL); Shalom Strano, Jerusalem (IL); Steve Krupa, Haifa (IL)

(73) Assignee: SPRINGLOC LTD, Hosen (IL)

( * ) Notice: Subject to any disclaimer, the term of this patent is extended or adjusted under 35 U.S.C. 154(b) by 439 days.

(21) Appl. No.: 18/083,565

(22) Filed: Dec. 18, 2022

(65) Prior Publication Data

US 2023/0120638 A1 Apr. 20, 2023

Related U.S. Application Data

(63) Continuation-in-part of application No. 17/841,663, filed on Jun. 16, 2022, now Pat. No. 12,232,861, (Continued)

(51) Int. Cl.
*A61B 90/00* (2016.01)
*A61B 90/50* (2016.01)
(Continued)

(52) U.S. Cl.
CPC ............... *A61B 90/37* (2016.02); *G06T 7/73* (2017.01); *G06T 19/006* (2013.01);
(Continued)

(58) Field of Classification Search
CPC .............. A61B 90/37; A61B 2090/363; A61B 2090/365; A61B 2090/373;
(Continued)

(56) References Cited

U.S. PATENT DOCUMENTS 8,892,185 B2 11/2014 Chi Sing
8,973,584 B2 3/2015 Brander et al.
(Continued)

FOREIGN PATENT DOCUMENTS

EP 2996555 B1 10/2020
WO 2017066372 A1 4/2017

OTHER PUBLICATIONS

Final Office Action for U.S. Appl. No. 17/724,487 mailed Oct. 25, 2024.
(Continued)

*Primary Examiner* — Chao Sheng
(74) *Attorney, Agent, or Firm* — Ballard Spahr LLP (57) ABSTRACT

The combination of a marker system with binocular AR glasses to create a soft tissue procedure system used for surgery, biopsies, etc. A marker localization system is functionally integrated with augmented reality (AR) glasses. This soft tissue system can be applicable for AR surgeries in soft tissues involving mobile and static anatomies anywhere in the body, such as for example, breast, soft tissue, lungs, lymph nodes, liver surgeries, etc. By the placement of single or multiple markers and localizing the markers with a locator, such as a hand-held locator as a non-limiting example, the above-mentioned system provides a real-time intraoperative coordinate frame for the virtual projection of the markers (and the associated ROI) on/in the surgical field/biopsy field of view, using commercial off-the-shelf computer hardware (laptops, tablets, etc.) for the required image processing.

22 Claims, 7 Drawing Sheets

Related U.S. Application Data which is a continuation-in-part of application No. 17/724,487, filed on Apr. 19, 2022.

(60) Provisional application No. 63/293,643, filed on Dec. 23, 2021, provisional application No. 63/231,243, filed on Aug. 10, 2021, provisional application No. 63/218,973, filed on Jul. 7, 2021, provisional application No. 63/179,893, filed on Apr. 26, 2021.

(51) Int. Cl.
| | | |
|---|---|---|
| *G06T 7/73* | (2017.01) | |
| *G06T 19/00* | (2011.01) | |
| *H04N 13/239* | (2018.01) | |
| *H04N 13/344* | (2018.01) | |

(52) U.S. Cl.
CPC ......... *H04N 13/239* (2018.05); *H04N 13/344* (2018.05); *A61B 2090/363* (2016.02); *A61B 2090/365* (2016.02); *A61B 2090/373* (2016.02); *A61B 2090/3908* (2016.02); *A61B 2090/3945* (2016.02); *A61B 2090/502* (2016.02); *G06T 2207/10021* (2013.01); *G06T 2207/30096* (2013.01); *G06T 2210/41* (2013.01)

(58) Field of Classification Search
CPC .... A61B 2090/3908; A61B 2090/3945; A61B 2090/502; G06T 7/73; G06T 2207/10021; G06T 2207/30096; G06T 19/006; G06T 2210/41; H04N 13/344
See application file for complete search history.

(56) References Cited

U.S. PATENT DOCUMENTS

| | | | |
|---|---|---|---|
| 9,386,942 | B2 | 7/2016 | Chi Sing et al. |
| 9,646,423 | B1 | 5/2017 | Sun et al. |
| 9,713,437 | B2 | 7/2017 | Fullerton |
| 9,730,764 | B2 | 8/2017 | Van Der Weide et al. |
| 9,867,550 | B2 | 1/2018 | Brander et al. |
| 9,987,097 | B2 | 6/2018 | Van Der Weide et al. |
| 10,154,799 | B2 | 12/2018 | Van Der Weide et al. |
| 10,278,779 | B1 | 5/2019 | Rudie et al. |
| 10,326,975 | B2 | 6/2019 | Casas |
| 10,383,544 | B2 | 8/2019 | Fullerton et al. |
| 10,646,303 | B1 | 5/2020 | Strano et al. |
| 10,751,145 | B2 | 8/2020 | Van Der Weide et al. |
| 10,827,949 | B2 | 11/2020 | Greene et al. |
| 10,849,529 | B2 | 12/2020 | Brander et al. |
| 10,854,799 | B2 | 12/2020 | Tanabe |
| 10,970,862 | B1* | 4/2021 | Na ........................ A61B 34/10 |
| 2005/0279963 | A1 | 12/2005 | Church et al. |
| 2011/0021888 | A1 | 1/2011 | Sing et al. |
| 2014/0309522 | A1 | 10/2014 | Fullerton et al. |
| 2016/0051164 | A1 | 2/2016 | Derichs et al. |
| 2018/0125389 | A1 | 5/2018 | Brander et al. |
| 2018/0279907 | A1 | 10/2018 | Greene et al. |
| 2019/0150779 | A1 | 5/2019 | Derichs et al. |
| 2019/0223975 | A1 | 7/2019 | Agostinelli et al. |
| 2019/0365279 | A1 | 12/2019 | Fullerton et al. |
| 2020/0409306 | A1* | 12/2020 | Gelman ............... G02B 27/017 |
| 2021/0100476 | A1 | 4/2021 | Brander et al. |
| 2021/0169579 | A1 | 6/2021 | Laviola et al. |
| 2022/0338953 | A1 | 10/2022 | Strano et al. |

OTHER PUBLICATIONS

Non-Final Office Action for U.S. Appl. No. 17/724,487 mailed Apr. 11, 2024.

Non-Final Office Action for U.S. Appl. No. 17/724,487 mailed Feb. 12, 2025.

Notice of Allowance for U.S. Appl. No. 17/841,663 mailed Oct. 30, 2024.

Restriction Requirement for U.S. Appl. No. 17/841,663 mailed May 22, 2024.

U.S. Appl. No. 17/724,487, filed Apr. 19, 2022.
U.S. Appl. No. 17/841,663, filed Jun. 16, 2022.
U.S. Appl. No. 63/179,893, filed Apr. 26, 2021.
U.S. Appl. No. 63/218,973, filed Jul. 7, 2021.
U.S. Appl. No. 63/231,243, filed Aug. 10, 2021.
U.S. Appl. No. 63/293,643, filed Dec. 23, 2021.

"FCC Online Table of Frequency Allocations", Federal Communications Commission Office of Engineering and Technology Policy and Rules Division, Jul. 1, 2022, pp. 1-180.

"LOCalizer Wire-Free Guidance System", Hologic Inc. Breast Surgery Portfolio https://hologicbreastsurgery.com/en/portfolio/localizer-wire-free-guidance-system/ last accessed Jan. 28, 2025, pp. 1-3.

"NTAG 203 NFC Forum Type 2 Tag Compliant IC With 144 Bytes User Memory", NXP Semiconductors; Product Data Sheet Rev. 3.0; https://cdn-shop.adafruit.com/productfiles/4034/P4034_datasheet_NTAG_203.pdf last accessed Jan. 28, 2025, Oct. 17, 2011, pp. 1-30.

Harrison, et al., "A 60 GHz Analog Phase Shifter in 65 NM Bulk CMOS Process", International Journal of Computer Networks & Communications (IJCNC); vol. 2, No. 4, Jul. 2010, pp. 13-20.

Stolik, et al., "Measurement of the Penetration Depths of Red and Near Infrared Light in Human "Ex Vivo" Tissues", Journal of Photochemistry and Photobiology B: Biology; vol. 57, Issues 2-3, Sep. 2000, pp. 90-93.

Yan, et al., "Optimization of Output Power and Transmission Efficiency of Magnetically Coupled Resonance Wireless Power Transfer System", AIP Advances; Research Article, Magnetism and Magnetic Materials https://doi.org/10.1063/1.5007276 last accessed Jan. 28, 2025, Jan. 2, 2018, pp. 056625-1-056625-6.

* cited by examiner

AUGMENTED REALITY SOFT TISSUE BIOPSY AND SURGERY SYSTEM

CROSS-REFERENCE TO RELATED APPLICATIONS

This is a utility patent application being filed in the United States as a non-provisional application for patent under Title 35 U.S.C. § 100 et seq. and 37 C.F.R. § 1.53(b) and, claiming the benefit of the prior filing date under Title 35, U.S.C. § 119(e) of the United States provisional application for patent that was filed on Dec. 23, 2021 and assigned Ser. No. 63/293,643, further, this application is a continuation-in-part of U.S. patent application Ser. No. 17/841,663, which was filed on Jun. 16, 2022 and claiming the benefit of the prior filing date under Title 35, U.S.C. § 119(e) of the United States provisional application for patent that was filed on Jul. 7, 2021 and assigned Ser. No. 63/218,973, which is a continuation-in-part of U.S. patent application Ser. No. 17/724,487, which was filed on Apr. 19, 2022 and claiming the benefit of the prior filing date under Title 35 U.S.C § 119(e) of the United States provisional application for patent that was filed on Aug. 10, 2021 and assigned Ser. No. 63/231,243 and the United States provisional application for patent that was filed on Apr. 26, 2021 and assigned Ser. No. 63/179,893, each of the above-identified applications are all incorporated herein by reference in their entirety.

BACKGROUND

Field of Invention

The present invention described herein is related to the field of biopsy and surgical navigation systems or, more specifically, devices for guiding surgeons in real time, intra-operatively, to locate and remove non-palpable, non-visible markers and associated embodiments of soft tissue for example at breast surgery and for augmented needle biopsy of tissues under image guidance.

The technical area that utilizes augmented reality (AR) systems as an approach to assist in the performance of activities or task, can cover a wide range of implementations. As a few non-limiting examples, AR systems may utilize heads-up displays (HUD) combining augmented information that is not correlated with visual geometry. As another example, AR systems my utilize augmented information that is correlated with visual objects. Even further, AR systems may utilize computer-synthesized images combined with actual visible scenes. The latest AR systems require special augmented reality glasses, generally comprising a binocular optical system realized using a pair of high-definition video cameras and a pair of high-resolution color displays. Recent advances in image processing, both hardware (HW) and software (SW), have provided computational speeds needed to truly implement AR systems in real-time, allowing for precise geometrical alignment of visual and computer-synthesized objects at distances appropriate for surgeries.

Recently developed apparatuses and methods of augmented reality have described navigation and guidance techniques in different surgical settings such as: spinal surgeries (U.S. Ser. No. 10/326,975B2), brachytherapy (U.S. Pat. No. 9,646,423B1), cerebral aneurysm (WO2017066372A1), minimally invasive operations (U.S. Pat. No. 9,646,423B1), etc. Most of these methods are based on pre-operative Magnetic Resonance Imaging (Mill) and 3D Computerized Tomography (CT) studies of the relevant Regions of Interest (ROI's) of anatomical regions requiring surgical intervention with the generation of relevant 3D reference images. These 3D studies can act as templates for image fusion in AR systems.

A large percentage of soft tissue tumors, such as for example breast cancers, are not visible or palpable to the surgeon at the time of surgery. Until recently, a surgeon performing such procedures has had to rely on other localization technologies to guide the surgeon to the ROI in which the tumor to be excised is located. These prior art localization techniques include technologies such as guide wires and varying marker types. Some markers are combined with an accompanying localization system to assist in their detection. These markers may be referred to as smart markers. The current systems are lacking in that while they guide the surgeon to the ROI to be surgically removed, they only approximate the ROI. Further, the current systems do not provide the surgeon with direct sight of the markers and the ROI nor a visual picture of the placed markers and ROI requiring excision.

The prior art includes marker localization systems that operate to allow markers to be localized with a hand-held locator. However, these systems lack intermarker connectivity. These are discrete single marker localization events suitable for small discrete lesions closely associated with their marker. In instances where a region/volume of tissue (ROI) requires multiple markers to define its margins (bracket localization), current systems require the localization of each marker as a separate event. Unfortunately, such prior art systems result in creating an ambiguity in the determination of the edges of the tumor volume. Thus, the surgeon is still required to imagine the shape/extent of the ROI and the individually placed markers associated with it. Of note, many currently used markers create a significant artifact during MRI imaging. This artifact is highly problematic in instances where markers are still in vivo at sites requiring follow up MM, for example in a neoadjuvant setting.

The application of augmented reality (AR) for breast surgery is especially challenging. The breast, as an organ, can be examined with MM (usually in the prone position) or CT (supine position but with the patients arms usually above their heads) with the generation of 3D images. However, these studies are performed in positions entirely removed from the position of the breast as presented during surgery. Because breast tissue is flexible and often pendulous, there is a dramatic change in tissue orientation between the imaging study/capture positions and the surgical position. In short, the preoperative 3D images of the breast simply cannot act as an accurate template for image fusion augmented reality in the setting of breast surgery. This problem is compounded in the neoadjuvant setting where the tumor has been treated prior to surgery and is no longer visible at post treatment imaging for example at Ultrasound and Mill. In such instances there is no visible tumor for image fusion.

In cases where a tumor at imaging has fully responded (complete imaging response) or almost fully responded to preoperative therapy (neoadjuvant therapy), there can be a need to biopsy the original tumor bed in order to establish if there is indeed residual tumor present (ie, complete pathological response). The accurate sampling/biopsy of a soft tissue area previously involved or now minimally involved by tumor where the tumor is no longer seen or not clearly seen at imaging for example at Ultrasound, can be challenging. In the event of complete pathological response, there may be no need for further surgery.

There is therefore a pressing need to overcome the current shortfalls described above by developing a system whereby augmented reality can be reliably and accurately employed in the setting of soft tissue lesions/tumors requiring biopsy and or surgery especially in a mobile tissue environment, for example in the breast. Marker systems, whereby a marker/s placed within the relevant soft tissue in association with a ROI and detected and triangulated with the aid of a locator/detector, provide a potential solution to this problem. Current marker technologies do not provide sufficient data for the needs of the surgical and support teams. Moreover, these systems lack the computing ability to transform the localization process into data appropriate for augmented reality assisted biopsy and/or surgery.

Furthermore, there is a need for a system of MRI compatible markers of non-ferrite material without significant MRI artifact, with inter-marker connectivity.

BRIEF SUMMARY

The terms "physician", "operator", "surgeon", etc., as used herein, are understood to be a person performing an appropriate procedure within the context of relevant activity and will be understood to be used interchangeably and generally throughout this document.

The term "surgical instrument" includes surgical instruments used in a surgical procedure, such as but not limited to, surgical knives, diathermy instruments, retractors etc. as well as biopsy needles, ablation device needles, radiation needles etc. These terms will be understood to be used interchangeably and their meaning will be generally understood from the context.

The term soft tissue will be used generally and will be understood to be any soft tissue in the body, such as the breast and axillary tissue as non-limiting examples. Likewise, the term breast will be understood to be representative of other soft tissues in the body.

The combination of a smart marker localization system with binocular AR glasses and a processing device (computer and associated SW) is the basis of the current disclosure. The various invention embodiments may utilize the marker system described in U.S. patent application Ser. No. 17/841,663, which was filed on Jun. 16, 2022 and hereinabove incorporated by reference (the '663 application), integrated with augmented reality (AR) glasses. This system can be applicable for AR surgeries in soft tissues involving mobile and static anatomies anywhere in the body, such as for example, breast, soft tissue, lungs, lymph nodes, liver surgeries, etc. By the placement of multiple markers and localizing the markers with a locator, such as a hand-held locator as a non-limiting example, the above-mentioned system provides a real-time intraoperative coordinate frame for the virtual projection of the markers (and the associated ROI) on/in the surgical field/biopsy field of view, using commercial off-the-shelf computer hardware (laptops, tablets, etc.) for the required image processing. Various types of surgical markers may be utilized. Passive surgical markers include, reflectors of signals, etc., while others are activated. The present invention focuses on activated smart markers that are transponders, although aspects and embodiments of the invention may also utilize other passive type makers. The passive markers used for localization may be referred to as multimodality markers belonging to multimodality systems and can be broadly divided into the following groups:

1. Magnetic Reflectors—such as Magseed and Molli, these are magnetic seeds that merely reflect back the sent signal.
2. Radar reflectors—such as Savi Scout, which are responsive to an infra-red signals.
3. Activated markers—RFID markers activated by an appropriate RFID code signal like Elucent and Health Beacons LOCalizer and other markers, such as those described in the '663 application, activated by a modulated electromagnetic signal.

An important difference between Elucent and Health Beacons LOCalizer and the '663 application markers is that the former two are detected by the change in amplitude between the sent and received signal whereas the '663 application markers are ferrite free transponders and are detected by the phase shift in the signals. The method of this locator system is described in the '663 application.

Smart markers placed prior to systemic therapy (neoadjuvant therapy) and rendered by AR can assist, especially in cases of complete imaging response, in defining original tumor area(s) requiring image guided biopsy for example at ultrasound.

Smart markers with associated appropriate localization devices (including handheld, remote or robotic locators etc.), which provide the distance between the locator tip and the in vivo markers (depth) can also be integrated in exemplary embodiments of the AR system.

The term "locator" will be used generally and is understood to represent a locating device appropriate for the localization of a marker belonging to the appropriate 'locator marker system'.

Binocular optical glasses can be used as a platform for precise geometrical measurements allowing remote coordinate estimations of point objects. The provided factory calibrations of current AR glasses systems allow for nearly ideal measurements, limited only by the quantization (resolutions) of the provided optical matrix (cameras and displays).

A surgeon can perform a biopsy/operation using AR glasses during the entire procedure. The glasses have a binocular pair of real-time video cameras and a pair of video displays all integrated with an augmented reality SW program running on a tablet/laptop computer and coordinating the activities of the marker system. The AR features and logistics are achieved in real-time as the surgeon proceeds from seeing the projected markers on/below the patient's skin surface to seeing the virtual image of the markers projected within the deeper tissues of the dissection and the operative field. The virtual position of the markers can be simultaneously coordinated with the virtual position of the ROI. The described process can be realized seamlessly, so as to fit with the current workflow of marker placement and surgery. The method does not require preoperative 3D imaging of the ROI and image fusion for AR. After marker implantation, the orientation of the marker(s) relative to the ROI(s) can be verified with an imaging modality relevant for each instance such as Ultrasound, X-ray, mammography, CT and MiII. The markers can be placed via an introducer needle or manually with a clip or stich as non-limiting examples.

Following this verification of the orientation of the marker(s), the surgeon can determine the positions of all of the markers sequentially, one by one. This process is performed interactively by gliding the locator, which can be handheld along the surface of the patient's tissue, for example the breast. Feedback can be provided acoustically (by changing the audio tone as a function of distance) and visually via the AR glasses. One possible GUI (Graphic User Interface) example presents the ID of the currently selected marker, the distance (such as in mms) from the locator tip to this marker, and a projected circle around the tip of the marker whose radius equals said distance. In some embodiments, the markers may include collective ID's which show a relationship between the markers. In a particular embodiment, the collective ID of a marker is a combination of at least two identifying features unique to a marker including features visible on an imaging modality such as mammography. One of these ID features can be a unique electronic ID. The collective ID of each marker is identified as being unique and different from the collective ID of other placed markers. The concept of collective marker ID is described in detail in US 2022/0338953 and in U.S. Ser. No. 17/841,663. The sector of "correct" direction can be emphasized as well. The exact position on the relevant tissue surface/skin overlying each marker is determined as the location of minimum measured distance between the tip of the locator and the marker (i.e, the optimal approach vector). The surgeon can indicate/signal that he has completed the detection of each marker. The position of the marker is stored in the XYZ coordinate system relative to the AR glasses. The origin of the system is located at the mid-point between the optical sensors of the glasses. The position of the locator tip serves as a reference point for the process. Following the localization of the first marker, the system is switched (automatically or manually by the surgeon) to another marker, and the localizing process is repeated. Upon successfully localizing the second marker, the system stores the position of this new (currently selected) marker and the distance from the currently selected marker to the previously selected marker. This process can be applied to differing smart marker types as described above.

The process is continued until the last marker of the group is successfully localized, thereby defining the specified ROI. The last location of the locator's tip (i.e., the optimal approach vector for the last detected marker of a group of markers), can be assigned as a binocular optically visual first reference point suitable for the AR operation. Once this process is completed, the AR system can display the pattern of markers surrounding the ROI as a virtual projection overlaid upon the optically visual surgical scene.

Localization of the last marker can render the AR scene. At localization of the last marker, the surgeon defines the above-described first reference point and can indicate/signal that he has completed the detection of the last marker and relevant markers defining the ROI. The reference point is the geometrical mid-point (centroid) between the markers' projections on the tissue surface for example the skin. Touching this point with the tip of the locator and signaling of this event to the computer creates a 3D connectivity mesh (realized for example as a wired pyramid) in the memory of the computer. The base of the pyramid is composed of the markers' projected positions, while its summit is defined by the vector linking the reference position to the locator's tip. All lengths of wires (ribs) defining the pyramid are determined during the markers' localization. On completion of the above-described marker localization process, the computer can display to the surgeon, via the AR glasses, the ROI reference point on the relevant tissue surface—for example the skin of the breast. The mentioned ROI reference point can be drawn/marked on the skin/tissue using some unique high contrast color/icon or by placing an inert visual clip or high contrast object. This reference point on the skin may however lie in an area requiring skin removal or surgical entry. In such instances, further multiple auxiliary reference points in the vicinity of the ROI can be chosen and designated on the skin/tissue surface and assigned for example with sterile ink or with a physical marker such as a clip or high contrast object. The extra reference points are assigned, for example by using the following described technique.

First, the locator is moved over the surface of the breast to an appropriate point outside the surgical dissection field. Once an appropriate point is chosen, a signal is sent from the locator to the computer to define the position of the chosen reference point. A plurality of reference points can be designated. These reference points are correlated with the marker's xyz positions already stored in the computer memory. A minimal number of reference points on the skin surface enables full 3D AR image rendering and continued marker localization. The locator which can be handheld can be temporarily removed. Real-time video cameras track the position of the reference point(s) relative to the markers' positions and provide feedback to the computer system throughout the procedure. In the event that there has been significant movement of tissue, for example as a result of the dissection and mobilization of tissue, the locator can be re-employed and the process described above can be repeated to define a new reference point and hence a new virtual rendering of the markers. Throughout the surgery, movement of the surgeon's head will move and rotate the projection of the markers as a dynamic AR scene, freeing both hands of the surgeon to perform the required surgical task(s). The virtual 3D pyramid can be seen as appearing within the breast tissue below the skin. The surgeon can via an appropriate interface switch from an augmented reality mode to an ordinary vision mode whereby he can operate with 'normal vision' through the AR worn glasses and vice versa.

The stereo image in the AR glasses facilitates a precise determination of tumor edges as defined by the placed markers thereby improving the surgical treatment by reducing collateral tissue damage. As stated, embodiments of the present system do not require preoperative 3D image fusion. However, the AR method of image fusion, for example using CT, MIll templates, can be incorporated as an add on to various embodiments of the system and method of the present invention.

The form and size of the virtual object (created by the placed markers) can be correlated with medical images (verification images) performed prior, at the time of and after marker implantation. In the event that the implanted markers adequately define the diagnosed tumor volume/ROI denoted for surgical removal, the virtual object can be established using appropriate assistance SW. An envelope wired 3D geometry figure with nodes determined by the marker locations is created. There can be cases where the verification images show that the markers have failed to adequately define the ROI. For instance, in such situations some suspicious regions can be located outside the marker envelope. In such cases, the virtual object of the multi-marker volume can be defined as a standard geometry volume, such as a cube, parallelepiped, sphere or ellipsoid, etc., whose dimensions are defined so as to envelope the fitted marker 3D points, with a spare scaling factor provided to complete coverage of the ROI.

The creation of the virtual object can be based on a single marker. In cases of a discrete small ROI, a single implanted marker can be sufficient for its designation and removal. In such cases, a virtual object of varying geometry can be chosen by the operator. The geometry of the virtual object can be a sphere around the marker. The diameter of the spherical virtual object can be determined by measurements derived from post marker implant, pre-surgical imaging studies such as Ultrasound, Mammography, CT, MM, etc. The position of the center of this virtual object can be defined by the position (XYZ-coordinates) of the marker. The desired appropriate measurement can be entered by the operator for example into a computer program which defines for example the size of the sphere as seen virtually at surgery.

Additionally, surgical instruments can be used as part of AR scene. After the determination of the system of reference points on the skin surface above the surgical ROI, the required instrument can be used in a manner similar to the locator. For this purpose, the instrument can have two light sources (for example point LED sources) attached, for example, to the top end and mid-point of instrument. The arbitrary length of the instrument can require a calibration procedure. Appropriate SW allows for the calculation of the XYZ-coordinates of the tip of the instrument touching the skin on the basis of estimation of the LEDs light points at the upper parts of the instrument. These point coordinates are measured by the binocular optical system of the AR glasses at the time of calibration.

Additionally, other interventional devices, such as for example but not limited to, biopsy devices, such as core needles and vacuum assisted biopsy needles, can be used as part of AR scene. After the determination of the system of reference points on the skin surface above the ROI, for example, the post systemic therapy, neoadjuvant treated tumor bed with questionable residual tumor cells, the required biopsy device/instrument/needle can be used in a manner similar to the locator. For this purpose, the device/instrument/needle can have two light sources (for example point LED sources) attached for example to the top end and mid-point of the needle. The arbitrary length of the needle can require a calibration procedure. Appropriate SW allows for the calculation of the XYZ-coordinates of the tip of the needle touching the skin on the basis of estimation of the LEDs light points at the upper parts of the instrument. These point coordinates are measured by the binocular optical system of the AR glasses at the time of calibration.

Similarly, the AR rendering of the tissue volume defined by markers can also be used for guiding other devices, such as for example, an ablation device or local radiation device, including in the form of a needle, into the correct area. For example, such capability is beneficial in cases where the tumor has responded to preoperative therapy and is no longer visible at imaging.

The combination of the system of marker coordinates together with reference points and the coordinates of the tip of the surgical instrument creates the virtual object of the dynamic field of operation. This virtual object is combined (by appropriate SW) with the binocular AR glasses worn by the surgeon. This combination creates an AR dynamic field of operation allowing the surgeon full visual control of the entire ROI. The described combination can allow the surgeon to see if the tip of his instrument(s), for example the cutting diathermy or scalpel, has 'entered' the virtual volume of tissue as defined by the markers and hence, transgressed the desired surgical margin. This transgression can also be indicated by a signal, such as for example, by a warning sound or a red (transgression) or green (non-transgression) light. By including the surgical instrument as described above in the AR scene, the surgeon is able to operate in real-time, seamlessly, without the need to periodically revert to using the locator. The surgical instrument can be seen in 3D with respect to the AR defined ROI. For example, the instrument can be seen or designated as lying anterior or posterior to the 3D wired virtual marker defined object.

The combination of the system of marker coordinates together with reference points and the coordinates of the tip of a biopsy needle can create the virtual object of the dynamic field for biopsy of the tumor bed. This object is combined (by appropriate SW) with the binocular AR glasses worn by, for example, a breast imager. This combination creates an AR dynamic field allowing the operator full visual control of the entire ROI as defined by the marker(s). The biopsy of the suspected residual tumor bed can be done with/under imaging for example ultrasound guidance. The described combination can allow the physician/operator to see, for example at real-time ultrasound, if the tip of the biopsy needle has 'entered' the virtual volume of tissue as defined by the markers or transgressed the desired originally defined tumor volume. This transgression can also be indicated by a signal, such as for example, by a warning sound or a red (transgression) or green (non-transgression) light. By including the biopsy device/needle/instrument as described above in the AR scene, the biopsy procedure can be performed seamlessly without the need to periodically revert to using the locator. The biopsy needle can be seen in 3D with respect to the AR defined ROI. For example, the needle/instrument can be seen or designated as lying anterior or posterior to the 3D wired virtual marker defined object.

One embodiment of the present invention is an augmented reality (AR) system for use in soft tissue procedures, such as surgeries, biopsies, or other procedures. The AR system includes a marker localization system that is used to guide the operator or use. The marker localization system includes one or more smart markers placed into a soft tissue region of interest of a subject prior to the performance of a procedure. Each of the placed makers are configured to respond to a signal. The marker localization system also includes a locator configured to be moved over a tissue surface of the soft tissue region of interest to detect signals from the one or more smart markers.

The AR augmented reality presentation of the surgical ROI is presented to the operator as a virtual object together with (surrounded by) the "real" image of the relevant soft tissue for example the breast. For the realization of this approach, a high-resolution binocular video system (HRBVS) is used to provide accurate measurements of the 3D positions of some contrast points located on a smart-marker localization locator, surgical instrument and on the surface of the breast (a physical reference point). Conventional smart-marker localization systems provide only the depth of the marker below the locator tip. The HRBVS system allows for the estimation also of the distance between markers, providing the 3D coordinates of each marker relative to the origin of the measurement system—ie, the point located mid-way between the two cameras of the binocular system. The same marker locator is used for the determination of the reference point on the skin of the breast. This point should also have strong visual contrast visualized by the HRBVS system during the entire surgery/procedure. The localization of this reference point is estimated by the optical system in the same geometry coordinate system as all other discrete points. Some scenarios, where exact measurements cannot be attained or relied upon, assumptions are made to get the most accurate results as possible. Any movement of the breast (for example by the surgeon) will not significantly change the distance between markers in the tissue of the breast and will not vary the distance between the markers and the reference point(s). Therefore, any movement of the reference point can be translated to the movement of markers. This assumption is used as the basis for tracking the invisible marker system by following the visible location of the reference point(s).

Embodiments of the AR system may include a smart-marker localization sub system, augmented reality (AR) glasses and an AR Computer System (or processing unit) with appropriate SW (i.e., the computer of the marker localization sub-system can also serve as the AR Computer or can interface with the AR computer) and visible/optically contrasted signs/icons. Each one of the above components of our system has its own structure and function. The structure of the smart-marker localization sub-system provides real-time estimation of the depth of each marker (as described in U.S. Ser. No. 17/841,663).

The optically visible signs/icons can be high contrast objects such as for example small locally powered LED light sources; small stickers having a contrast visual pattern, for example, a chess pattern (collectively referred to as contrast elements). These signs can be used for creating; contrast visual points on the marker-localization hand-held locator, surgical instruments, or reference point(s) placed on the breast skin in the vicinity of surgery. The markings, objects, signs, icons, stickers are collectively referred to as optically contrast visual elements.

The AR glasses are comprised of virtual reality (VR) glasses with an additional high resolution binocular video sub-system. The point-targets of this sub-system can be assumed to be parts of these AR glasses. The binocular video sub-system provides dual-channel video information (sequence of binocular frame-images) to the computer system. The point targets are some high contrast visual points. These points can be realized by for example LED light sources or small patterns (like chess-patterns) located in the field of view of the binocular sub-system. The high-resolution dual screens of the AR glasses are used for visual feed-back to the operator.

The AR computer system manages all AR operations. It receives simultaneously binocular video stream data from the binocular system and marker depth information from the locator during the 'pre-cutting' session of the surgery. The marker depth information can be accepted by the AR computer from the marker-localization system computer (via some interface) if separate computer options are used. During the 'active part' of surgery only video data stream is used by the AR computer for managing the AR process. This video data from the binocular system is transferred to the computer by a wired or wireless interface. The output/results of the AR algorithms in the computer are passed to the dual screens of AR glasses via wired or wireless interfaces. Specific real-time SW runs in the AR computer and provides all required functioning.

The operations of exemplary embodiments of the AR system are different for the 'pre-cutting' and the 'active session' of surgery (a first mode of operation) (where surgical instruments, needles etc. are used). The 'pre-cutting' phase of operation of some embodiments of the AR system simultaneously uses the binocular video sub-system of the AR glasses and the marker localization sub-system to collect information during the 3D localization of the markers. The procedure (work-flow) of marker localization is similar to that described in our marker localization system patent application U.S. Ser. No. 17/841,663. The locator has at least two visual contrast points (for example LED or icon chess patterns) allowing for their detection by the binocular video processing SW (The contrast points being easily separated from the background image). The details of the measurement of the marker 3D localization is mathematically described herein in the detailed description of the current application. At the conclusion of the procedure of marker localization, the operator choses some point in the vicinity of the area of surgical/biopsy entry and designates it as the reference point for further use. The operator can touch this point and then assign it by a visually contrast icon for example a LED or chess pattern. During the 'pre-cutting' phase, the operator will see the field of operation through the AR glasses as a regular field of view (the breast, locator, his own hands etc.). At the end of this 'pre-cutting phase, the computer collects the sequence of the binocular video images. Each dual (binocular) image comprises the high contrast points (of the locator) together with the value of the marker depth for each marker sequentially. The contrast points are detected and its pixel position (together with the depth information) is processed according to the presented algorithm for calculating the 3D coordinates of each marker. The 3D coordinates of the reference point is calculated in the same manner. At this moment, the computer is able to create the virtual object of the operational ROI volume (based on marker positions) and to store it into the computer memory. The system can now signal to the operator about readiness for the surgery/biopsy etc.

During the transition to the 'active session' of surgery (a second mode of operation), the AR system continues tracking the reference point(s), the 3D positions of markers and the virtual object in real-time. During the 'active session' of surgery, the operator can use the surgical instrument(s) in a manner similar to the locator. Each surgical instrument should be assigned by at least two contrast points. The AR computer system creates a composite binocular sequence of images (a video). Each image (left and right) of the video comprises real-time acquired images of the external field of operation (breast skin, surgical instrument, surrounding etc.) together with synthetic projections of the virtual object of surgery ROI. Two (binocular) projections of this composite object which can be in a plurality of geometrical 3D figure(s), colored and properly shadowed, creates in the brain of the operator an augmented reality feeling displaying the operational ROI bellow the skin of the soft tissue/breast. Some additional SW can signal to the surgeon the relative position of the tip of the surgical instrument/s with respect to the ROI (correct or mis-direction, etc.). This concept can provide guided assistance during the course of the surgery. In exemplary embodiments, the AR system may include a processing device that is configured to receive signal measurements from the locator and to perform calculations required for the binocular AR glasses to present the region of interest. A variety of locator types can be used and in some embodiments the locator has at least 2 LEDs allowing determination of the tip of the locator on the tissue surface.

It will be appreciated that in some embodiments, the system provides marker tracking without the use of the locator by just using the physical reference points.

In other embodiments of the AR system the locator is a conventional biopsy needle/surgical instrument including two or more small-sealed clips each comprising a point-LED and a battery energy source for locating a working edge of the instrument and wherein the processing system within the AR system is configured to present within an augmented scene the real-time position of the working edge of the biopsy needle/surgical instrument during a procedure.

In other embodiments, the AR system is configured to project a virtual, variable density "point cloud" wherein a spatial extent and density of the virtual, variable density "point cloud" is inversely proportional to an estimated distance between a tip of the locator and a currently selected marker.

In other embodiments, the AR system is configured to project a virtual, variable density "arrow field" wherein a spatial extent and density of the virtual, variable density "arrow field" is inversely proportional to an estimated distance between a tip of the locator and a currently selected marker, wherein a presented arrow direction corresponds to the (algorithmically estimated) "right" or best direction of search (locator tip scanning) for the currently selected marker. This AR feedback can provide additional information for the surgeon in an unobtrusive and intuitive way, and greatly expedite the marker localization process.

The above-described methods are applicable to any anatomical tissue site including static and mobile anatomical soft tissue areas.

DETAILED DESCRIPTION OF VARIOUS EMBODIMENTS

The present invention, as well as features and aspects thereof, is directed towards providing a marker localization system with binocular augmented reality (AR) glasses that are communicatively coupled to a server that directs a procedure.

The disclosed AR system, which may be utilized in surgical settings, biopsy settings or other procedures, comprises a marker localization system with binocular AR glasses wire/wirelessly interconnected with at least one master computer or processing unit (server, tablet, laptop, etc.). The computer can be the computer of the smart-marker localization system which can run additional appropriate SW for control of the AR processes, a computer independent to the AR system (a sole AR computer) or combined AR computer and marker localization system computers with appropriate interfaces for automatically transferring the data of markers depth in real-time. The term AR computer can also be referred to as the AR master computer. Throughout the disclosure, the general term 'computer' will be understood to refer to either or a combination of the above computer systems.

The AR glasses can comprise an assembly of VR glasses and high-resolution binocular video cameras wherein both the binocular system and VR glasses have appropriate interfaces with the computer(s) allowing real-time operations. The system also includes optically contrasted objects/signs/icons. The computer can provide: the distance measurements from the currently selected marker to a locator (which may be handheld); the marker's electronic ID if available; and inter-marker distance as well as to perform all required AR calculations. Simultaneously, the AR glasses provide the visual information used for geometry measurements, geometry transformation and composite image creation. The reader is referred to reference "U.S. Provisional Patent Application No. 63/218,973 Filed on Jul. 7, 2021" now U.S. patent application Ser. No. 17/841,663 filed on Jun. 16, 2022 (incorporated herein above by reference) for a detailed description of an exemplary marker system that is suitable for various embodiments of the AR surgical system. It should be appreciated by those skilled in the relevant art that markers and locators of design other than what is described in U.S. Ser. No. 17/841,663 may also be used to construct a virtual rendering of the ROI. Generally, the markers and locator design should be such that they provide marker depth/distance from locator tip to marker measurements. For example, Cianna Medical Savi Scout, Health Beacons LOCalizer, Magseed, Elucent, and Molli markers and their appropriate locators can be used to generate the AR rendering of the ROI by, for example, attaching appropriate LED's to their locators (the locator in the case of Elucent being a surgical instrument). Grid/chess board references can also be used for this purpose.

Embodiments of the AR system utilize markers that are transponders, although in some embodiments markers that are signal reflectors or signal activated may also be used. Further, the transponder embodiment of the AR system operate to process the phase shift between the signals that are received from the markers and the reference signal rather than just the wave amplitude. In some embodiments, smart markers may be utilized that have collective ID's. Some embodiments of the AR surgical system utilize a pair of commonly available glasses and smart markers of various companies each covered by patents, combined with a control system to provide a unique AR surgical system. The various embodiments provide a solution for use in soft tissue surgery or procedures, especially in mobile tissue environments, such as breast surgery, where standard augmented reality image fusion is difficult. The various embodiments likewise provide a solution for image guided soft tissue biopsy, especially using ultrasound, in cases where the tumor has completely or almost completely disappeared after the use of some systemic therapy given prior to planned surgery. In such instances, there is a need to biopsy a tissue area previously occupied by the tumor, which is no longer visible, in order to see if microscopic remnants of tumor are still present.

Figure 1:
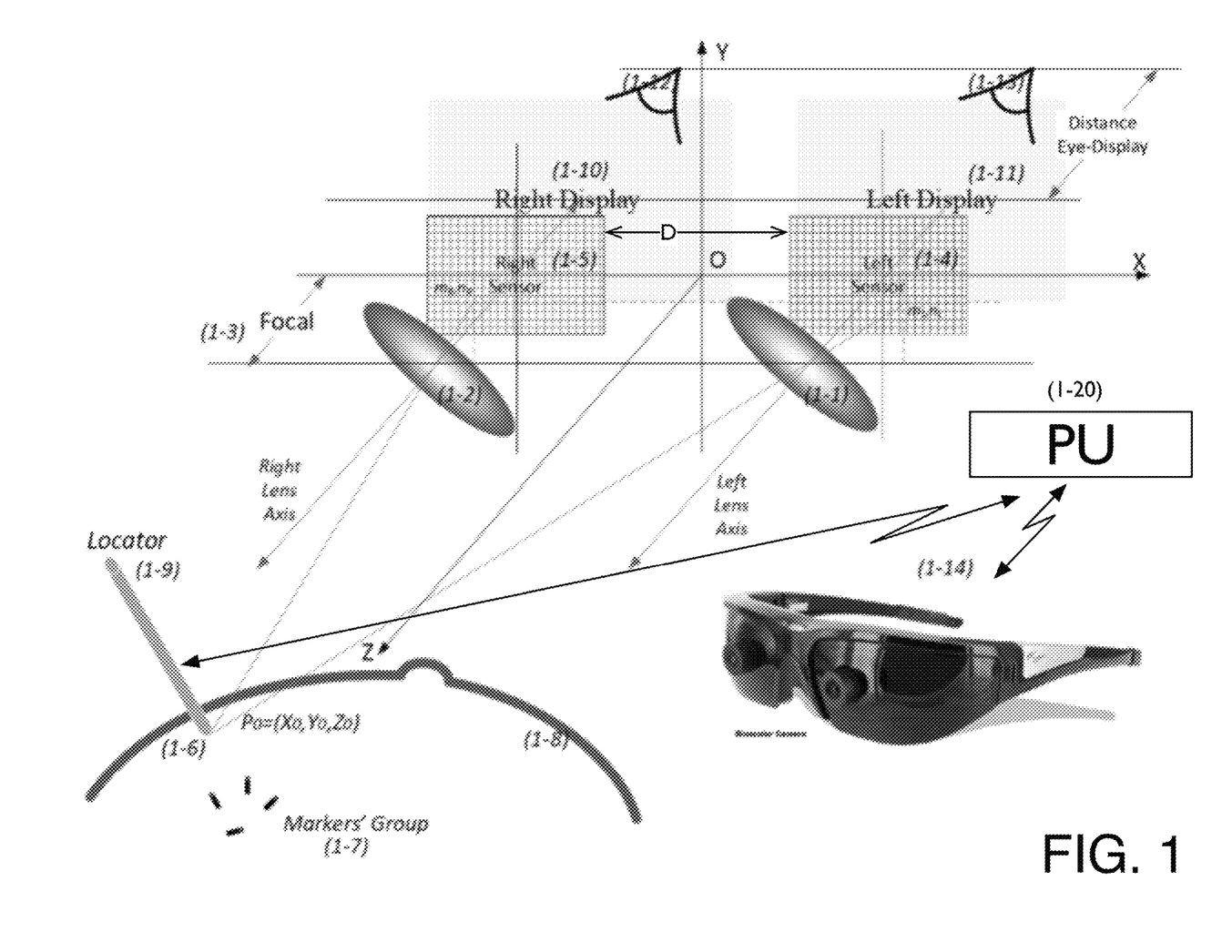
FIG. 1 is a conceptual diagram of a binocular system incorporating augmented reality with the main components of an exemplary AR system illustrated within a coordinate system.

FIG. 1 is a conceptual diagram of a binocular system incorporating augmented reality with the main components of an exemplary AR system illustrated within a coordinate system. In the illustrated binocular AR system (1-14), the left and right electro-optical subsystems (1-10) and (1-11)

respectively, are identical, comprised of the lens (1-1) (left) and (1-2) (right) located at their focal distance (1-3) from the video sensors (1-4) (left) and (1-5) (right). The left video sensor (1-4) being viewed from the left eye (1-12) and the right video sensor (1-5) being viewed from the right eye (1-13) from a particular distance. The coordinate system XYZ of the AR system has its origin O at the plane of the video sensors (1-4) and (1-5), placed at the mid-point between these sensors. The distance D between these sensors establishes the base of the binocular system. The rays from some point P0 (X0, Y0, Z0) (1-6) in soft tissue (1-8) housing a group of smart markers (1-7) create two different images at the left sensor (mL, nL) pixels and right sensor (mR, nR) pixels. Using the (known) sensor dimensions of locator (1-9) and pixel resolutions (which can be different in the x-axis and y-axis) we can calculate (reconstruct) the coordinates of point P0. In some embodiments a processing unit (1-20), which may be a desktop computer, laptop computer, mobile device, server, etc., is communicatively couple to the AR binocular glasses (1-14) and or the locator (1-9). The coupling may be wired or wireless in various embodiments. The processing unit (1-20) may be a computer or processing unit integrated with the smart-marker localization system and running additional appropriate SW for control of the AR processes. Similarly, the processing unit (1-20) may be a computer or processing unit that is independent to the AR system (a sole AR computer). Further, the processing unit (1-20) may be a combination of an independent AR computer and a marker localization system computer(s) with appropriate interfaces for automatically transferring the data of markers depth in real-time. Even further, the processing unit may be fully integrated within the AR glasses (1-14) or distributed between the AR glasses (1-14) localization system and/or an independent AR computer.

Figure 2:
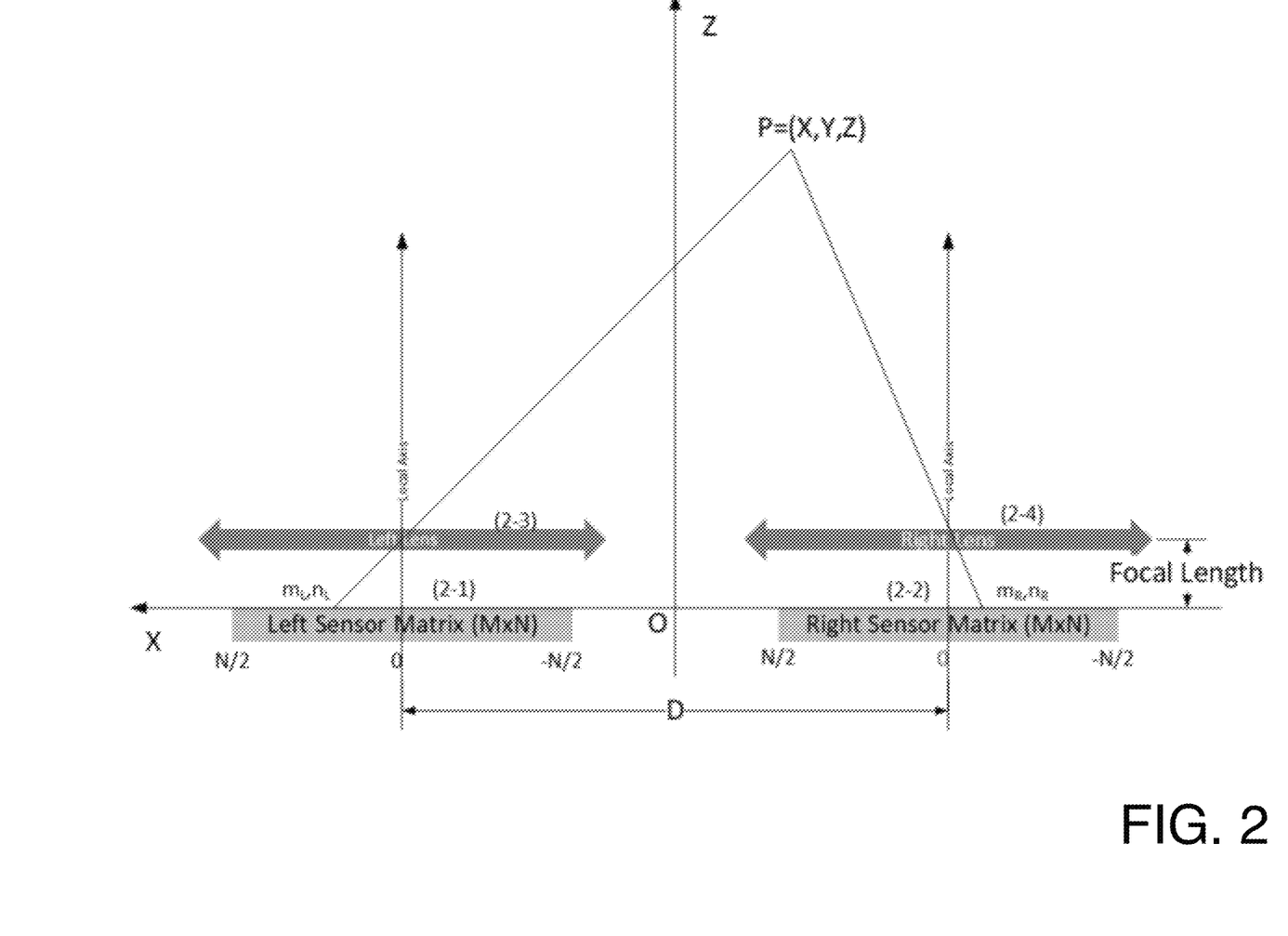
FIG. 2 is a diagram illustrating the binocular concept of remote measurements with simplified (2D) remote point localization.

FIG. 2 is a diagram illustrating the binocular concept of remote measurements with simplified (2D) remote point localization. The following algorithm can be demonstrated on the simplified 2D projection presented in FIG. 2:

The coordinate system XOZ has an origin at the middle between left sensor matrix (2-1) and right sensor matrix (2-2). The rays from the point P (X,Y,Z) pass through left lens (2-3) and right lens (2-4) to create images at the left matrix ($n_L$, $m_L$) pixels and at the right matrix ($n_R$, $m_R$) pixels. Both matrices are identical and have vertical number of pixels M and horizontal number of pixels N. In linear units of measure, the matrix resolutions are $\delta_X$ and $\delta_y$ respectively. The local origins of each matrix are at their centers, while the axises of local coordinate system of each one is:

Vertical: $m = -M/2, \ldots 0, \ldots M/2$, and

Horizontal: $n = -N/2, \ldots 0, \ldots N/2$.

The coordinates of point P can be calculated according to the following formulas:

$$X = \frac{D}{2} \cdot \frac{n_R + n_L}{n_R - n_L} \quad [\text{F 1}]$$

$$Z = \frac{D \cdot F}{(n_R - n_L) \cdot \delta_X} + F \quad [\text{F 2}]$$

$$Y = \frac{Z}{F} \cdot \frac{m_R + m_L}{2} \cdot \delta_Y \quad [\text{F 3}]$$

This binocular system, for example, has a base D=70 mm, focal lengths F=10 mm, sensor resolution of 20 MP (megapixels) and pixel size of 1.5 μm and provides an accuracy of X, Y, Z coordinate estimation of about 0.1 mm, at a distance range of Z=[300 to 500] mm. This range satisfies the distance from the eyes of the surgeon to the operation field for most surgeries including breast surgeries.

As described above, the AR process requires the surgeon to utilize the locator in the creation of the virtual image. For example, the surgeon can hold the locator and glide its tip across the tissue surface, for example, the patient's breast. The computer system provides accurate measurement of the distance between the tip of the locator and the marker-under-test. The tip of the locater can be (visually) obscured by the hands of the surgeon resulting in its coordinates not being optically measured directly by the AR system. This situation can require an estimation of the coordinates of the locator's tip.

Figure 3:
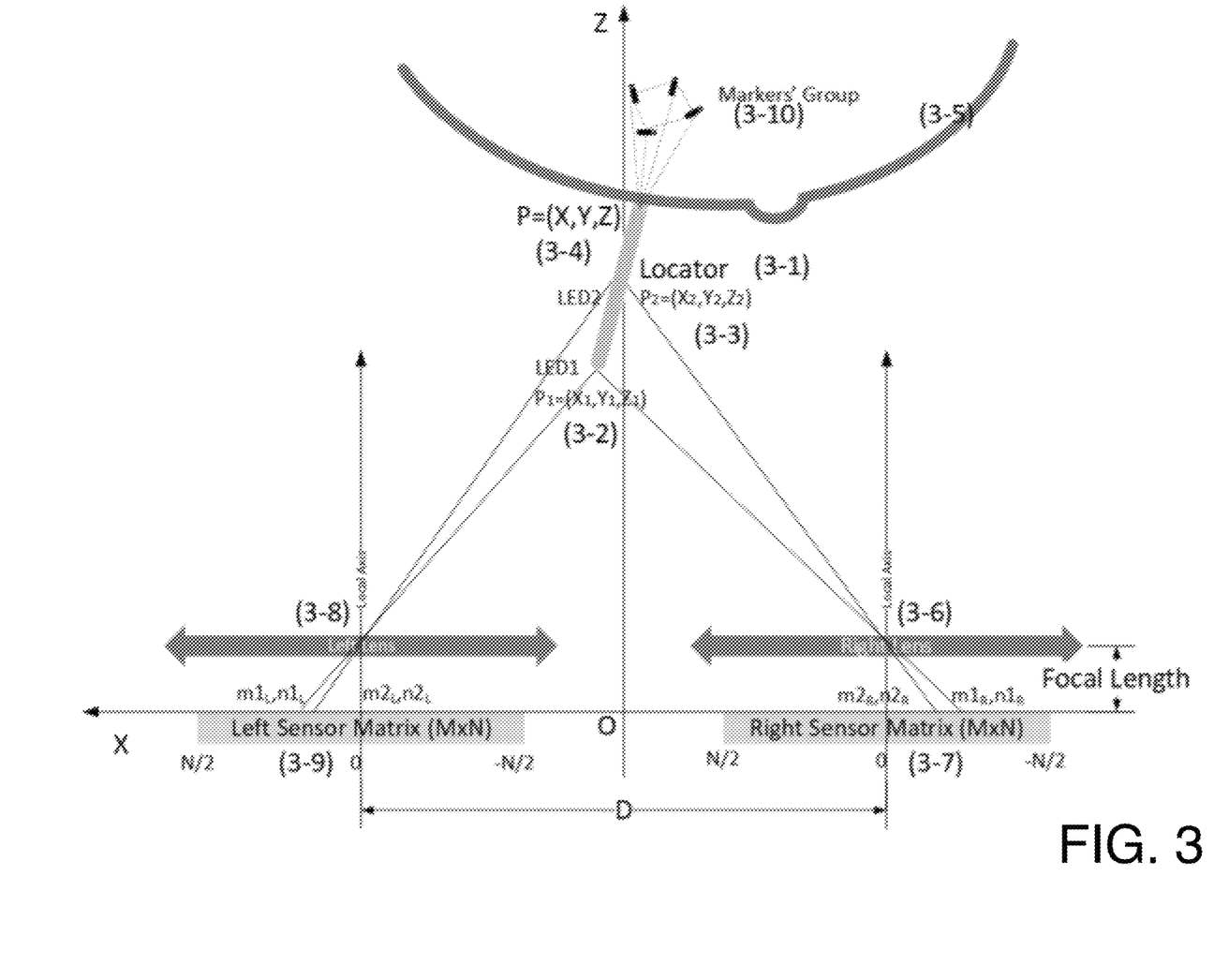
FIG. 3 is a conceptual diagram illustrating the estimation of the position of an "obscured" locator's tip, showing a method of determining the reference points and geometrically determining the markers' group (ROI) 3D object.

Estimation of the coordinates of the locator's tip is illustrated by FIG. 3. FIG. 3 is a conceptual diagram illustrating the estimation of the position of an "obscured" locator's tip, showing a method of determining the reference points and geometrically determining the markers' group (ROI) 3D object. Two LEDs can be used in the current disclosure to assign visible points on the Locator (3-1). One LED (3-2) can be located on the upper (visible) tip of the locator at the point P1=(X1, Y1, Z1). The other LED (3-3) can be located also on the visible part of the locator at P2=(X2, Y2, Z2). This point resides at a position a along the locator length L. The algorithm disclosed allows reconstruction of both points P1 and P2. In this case, the required point P=P(X,Y,Z) (3-4) of the locator's tip can be recalculated according to the following formulas for 2D solution:

$$k = \frac{Z_2 - Z_1}{X_2 - X_1} \quad [\text{F 4}]$$

$$X = X_1 \pm \frac{L}{\sqrt{k^2 + 1}} \quad [\text{F 5}]$$

$$Z = Z_1 \pm \frac{L \cdot k}{\sqrt{k^2 + 1}} \quad [\text{F 6}]$$

The solution is a point with maximum value of Z (most remote point from the AR origin). Due to the outside diameter of the locator body, a number of LEDs can be used around the body at point P2 to ensure an optically accessible (unobscured) visual point and allow for correct calculation(s).

The 3D estimation of the locator's tip position is performed according to the following algorithm:

Calculate the vector $V = P_2 - P_1$; [F7]

Calculate the Norm of the vector V:

$\text{Norm}(V) = \sqrt{(X_2 - X_1)^2 + (Y_2 - Y_1)^2 + (Z_2 - Z_1)^2}$; [F8]

Calculate unit vector $V_{UNIT} = V/\text{Norm}(V)$; [F9]

Find required point $P_3(X, Y, Z) = P_1 + L \cdot V_{UNIT}$. [F10]

The result of this algorithm can be verified:

$\sqrt{\Sigma_i^3 (P_3(\alpha_i) - P_1(\alpha_i))^2} = L$, where $X = \alpha_1, Y = \alpha_2, Z = \alpha_3$ [F11]

This algorithm provides an accuracy of 3D estimation of locator tip position to better than +/−0.2 mm.

The accumulation of marker localization data permits determination of the distances between the implanted markers and between the last localized marker and the tip of the locator. The combination of all these distances in the computer memory can be interpreted as a (3-5) 3D pattern, for example a pyramid as depicted in FIG. 3, extending from the marker group 3-10. This pattern within the computer memory is defined with respect to the last location of the locator's tip. This last location creates a reference point. The reference point can be designated on the relevant tissue, for example, the skin of the breast with an appropriate ink or marker. The pattern within the computer memory can be reinforced by choosing multiple reference points.

Figure 4:
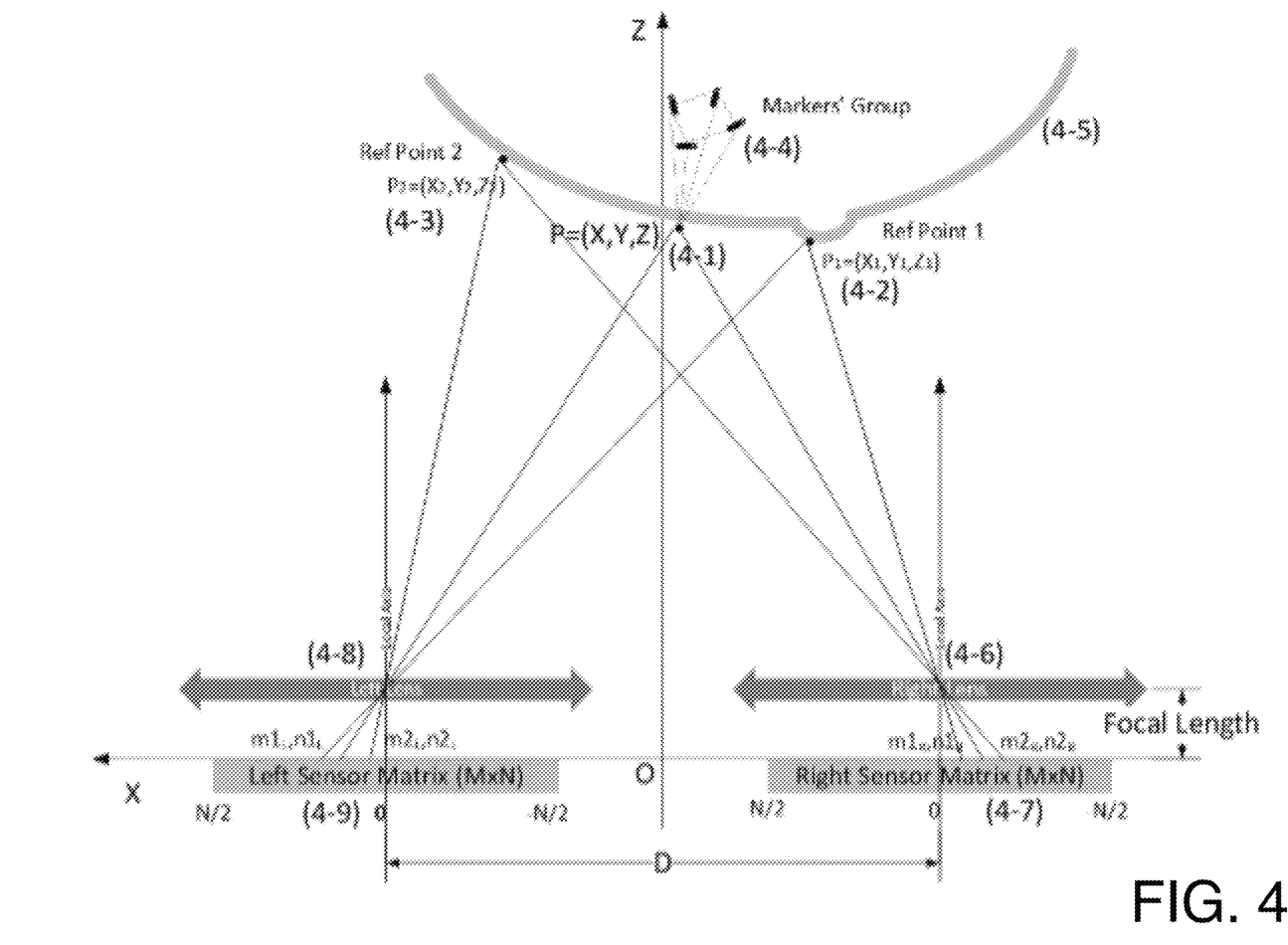
FIG. 4 is a conceptual diagram illustrating a virtual markers' group (ROI) determination, using the reference points alone rather than by using a locator for marker group tracking.

FIG. 4 is a conceptual diagram illustrating a virtual markers' group (ROI) determination, using the reference points alone rather than by using a locator for marker group tracking. Thus, the diagram of FIG. 4 illustrates the AR system measurements after removing the locator. Three reference points (4-1), (4-2) and (4-3) ensure localization of the "pyramid" 3D pattern (4-4) in the absence of the locator. Significantly, these three points should not lie on a straight line. Any movement or rotation of the AR glasses will cause a corresponding movement and rotation of the "pyramid" pattern, providing a spatially accurate (virtual) 3D visualization of the implanted marker group.

By performing the above-described process, the surgeon, after having set up a first marker pyramid, is free to operate on the markers and the ROI which they define with free hands and real-time vision. During the course of a surgery, for example with tissue mobilized and moved, the surgeon can at any time reestablish a new pyramid by relocating the markers and establishing a new ROI reference point. In the event of 3 or more markers being placed, the markers defining the base of the resultant 3D volume will determine the configuration/shape of that volume and the position of its reference tip.

Figure 5A:
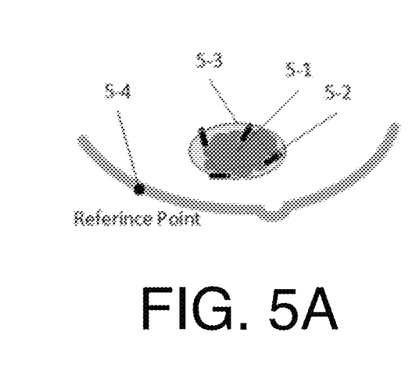
FIG. 5A is a conceptual diagram illustrating a group of markers establishing the shape of a virtual object defining a relatively large ROI volume to be removed.
Figure 5B:
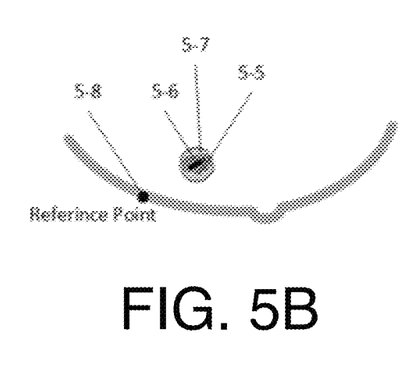
FIG. 5B is a conceptual diagram illustrating a single marker centrally located and establishing the shape of a virtual object defining a small ROI volume to be removed.
Figure 5C:
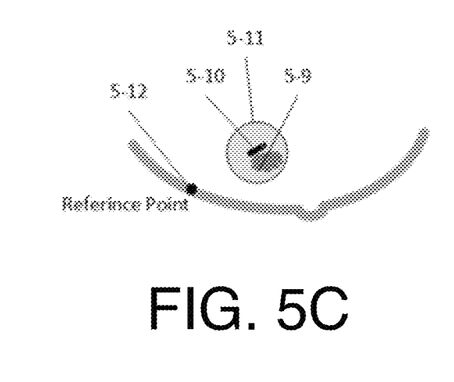
FIG. 5C is a conceptual diagram illustrating a single marker proximately located and establishing the shape of a virtual object defining a small ROI volume to be removed.

FIGS. 5A, 5B and 5C, collectively referred to as FIG. 5, illustrate the creation of differing examples of marker-assigned ROI's. FIG. 5A is a conceptual diagram illustrating a group of markers establishing the shape of a virtual object defining a relatively large ROI volume to be removed. FIG. 5B is a conceptual diagram illustrating a single marker centrally located and establishing the shape of a virtual object defining a small ROI volume to be removed. FIG. 5C is a conceptual diagram illustrating a single marker proximately located and establishing the shape of a virtual object defining a small ROI volume to be removed.

Looking at FIG. 5A, in the case of a relatively large volume of suspicious tissue (5-1), the markers can be implanted adjacent to the tumor edges (5-2). This is referred to as bracketing. If desired, a virtual object (5-3) of varying geometry can be fitted as an outer envelope surrounding the marker wired object. The fitted geometry can be parallelepiped, ellipsoid, spherical, etc. The position of this virtual object is defined by the XYZ-coordinates of each marker determined during the localization process described above. After localization of all markers of the virtual object, their position can be tracked optically (using the binocular sub-system of the AR system) relative to the reference point (5-4) also determined during the localization procedure.

Turning to FIG. 5B, in the case of a relatively small volume (for example diameter 1-2 cm) of suspicious tissue (5-5) or (5-9 in FIG. 5C), a single marker can be used for establishing the virtual object for surgery of the ROI. The elements (5-5)-(5-8) in FIG. 5B illustrate the case where the marker is implanted in the center of the suspicious volume (5-5), while element (5-9)-(5-12) in FIG. 5C depicts the marker implanted at the edge of the suspicious volume (5-9). In both cases, the single-marker can be used for defining the lesion. The chosen virtual object can be of a plurality of shapes, for example a sphere. The dimensions, for example the diameter of a virtual spherical object, are defined by the operator by inspection of the medical images of the implanted markers pre-surgery. The diameter of a spherical virtual object can be determined by measurements derived from post marker implant, pre-surgical imaging studies such as Ultrasound, Mammography, CT, MM, etc. For example, the position of the center of a spherical virtual object is defined by the position (XYZ-coordinates) of the marker. The desired appropriate measurement can be entered by the operator into a computer program which defines the size of the sphere as seen virtually at surgery or for example at image guided needle biopsy. The program can assign a plurality of shapes. The shapes may be irregular and assigned by an artificial intelligence (AI) interface based on tumor outline data from preceding diagnostic imaging such as MM, CT and Ultrasound. The operator can also elect to place the chosen virtual object shape eccentrically depending on presurgical imaging.

Figure 6:
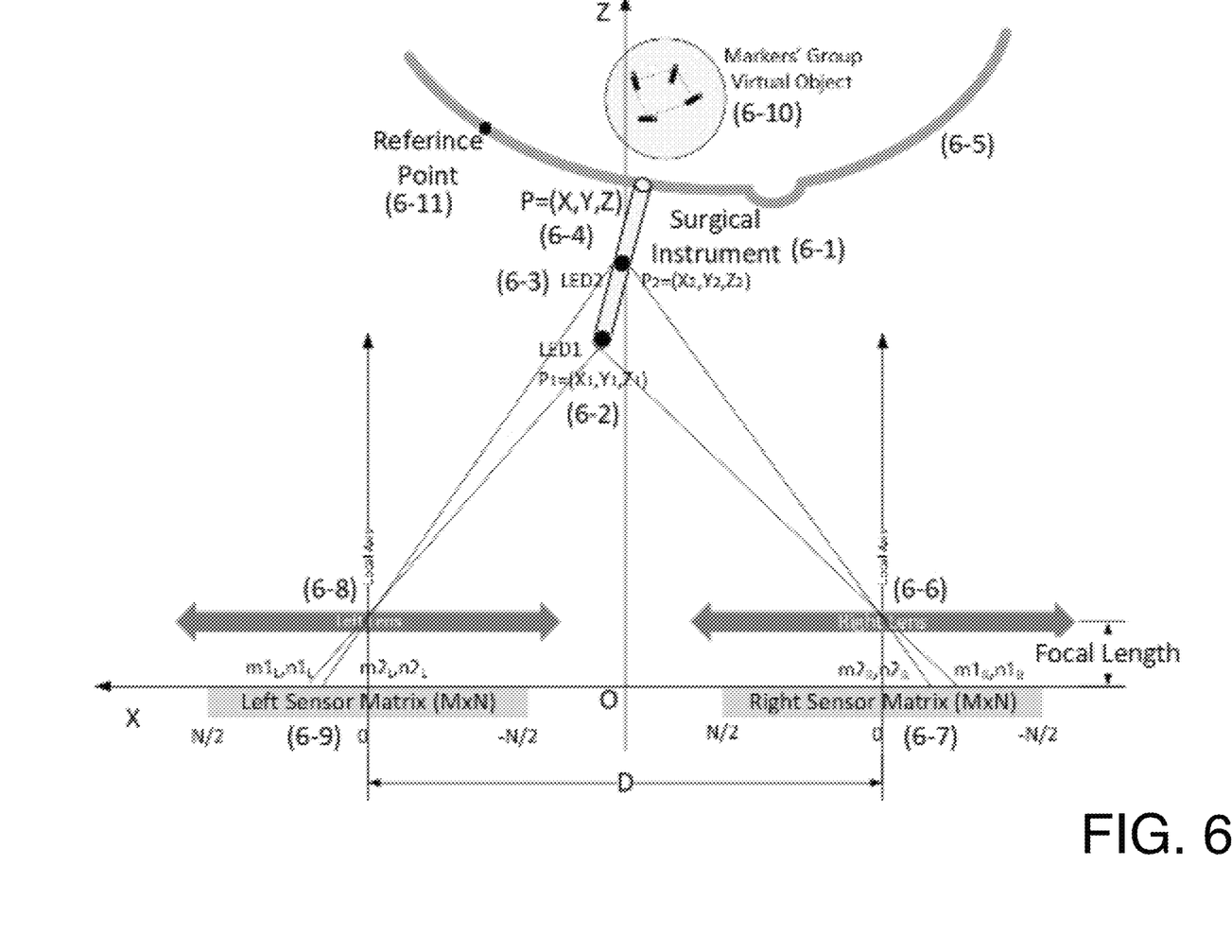
FIG. 6 is a conceptual diagram illustrating a virtual operational ROI virtual object created by the combination of smart marker volume and light defined surgical instrument (6-2) whose position is defined by at least one reference point (6-11).

FIG. 6 is a conceptual diagram illustrating a virtual operational ROI virtual object created by the combination of smart marker volume and light defined surgical instrument (6-2) whose position is defined by at least one reference point (6-11). Thus, the illustration depicts the creation of the Virtual operational ROI. FIG. 6 illustrates the creation of the combination of a virtual object composed of smart markers volume (6-10) and a light defined surgical instrument (6-2), whose locations are defined relative to at least one reference point (6-11). The surgical instrument (6-1) may be a biopsy needle device, ablation device needle or other interventional device, such as a local radiation device, as non-limiting examples. Similar to the estimation of the locator tip described above, the tip of surgical instrument (6-2) or other relevant device as described can be determined by the binocular system (6-6), (6-7), (6-8), (6-9), according to the equations [F4]-[F6] and algorithm [F7]-[F11]. The only difference is an unknown arbitrary length of the surgical instrument L. This value can be determined by the calibration procedure illustrated in FIG. 7.

Figure 7:
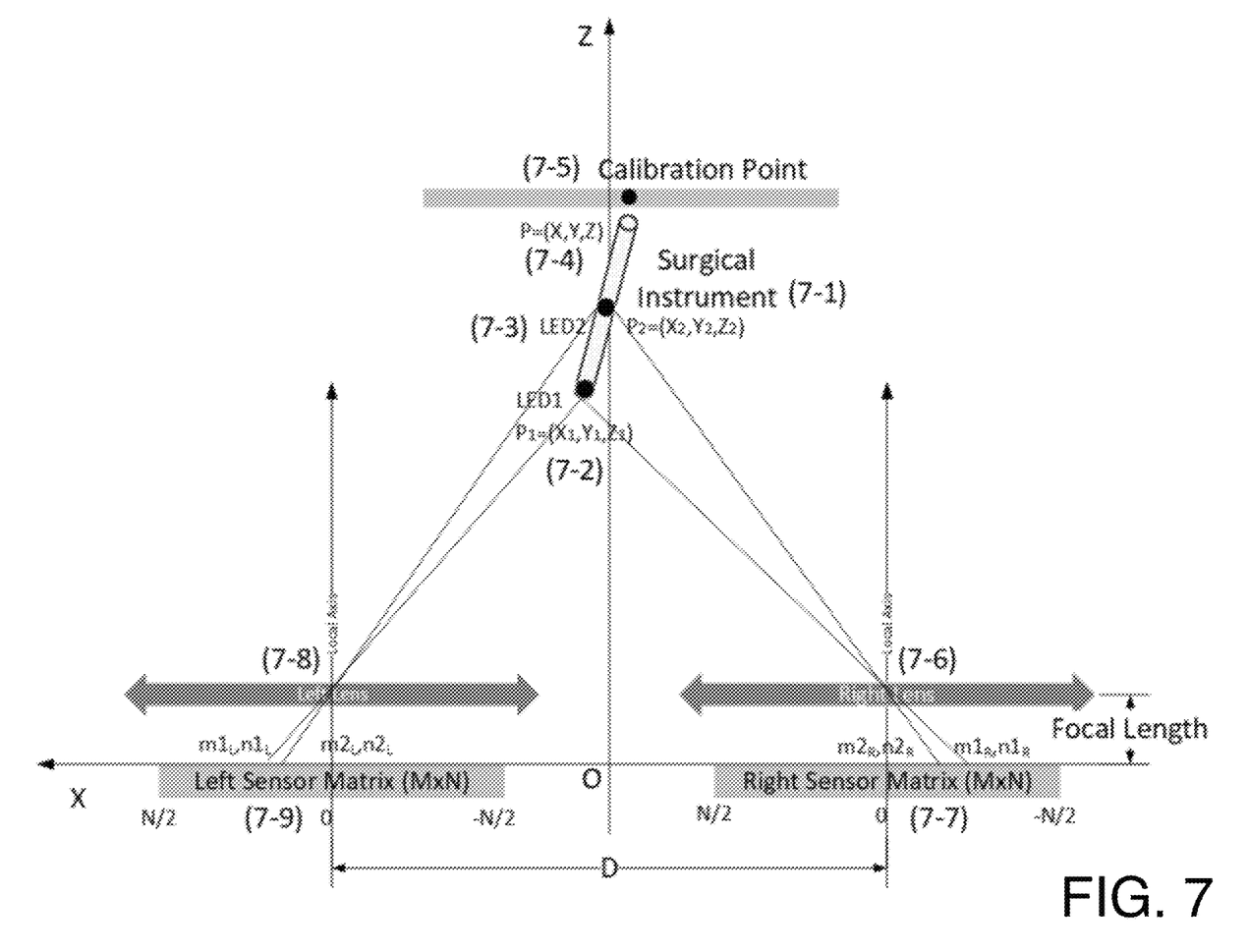
FIG. 7 is a diagram illustrating a procedure for calibrating a surgical instrument's length for use in AR surgery by touching the calibration LED (7-1) while being observed by the AR glasses.

FIG. 7 is a diagram illustrating a procedure for calibrating a surgical instrument's length for use in AR surgery by touching the calibration LED (7-1) while being observed by the AR glasses. The calibration of the length of the surgical instruments (7-1) can be used on instruments such as biopsy needle devices or surgical instruments. Biopsy needle devices/surgical instruments used in biopsy procedures for example, ultrasound guided biopsies and/or AR surgery can have attached two clips, for example, each composed of a sterile sealed mechanical assembly comprising a point-LED optical source and a small battery. One LED can be located at the upper tip of the needle/instrument (p1), while second one can be attached at the mid part of the needle/instrument (p2). The lower tip (p) of the needle/instrument can be free for biopsy/operating.

The calibration procedure can be performed prebiopsy/presurgery for biopsy needles and surgical instruments such as an electrocautery device, diathermy knife and scalpels etc, planned to be used in the course of the biopsy/surgical procedure. The calibration process uses a calibration point (calibration LED (7-5)) located on an appropriate calibration surface. The operator can touch the calibration LED and assign this event by sending a signal to a computer system designating the start of the appropriate calibration program. The binocular sub-system of the AR system performs an estimation of the 3D locations of 3 LEDs: $P_1$, $P_2$ and P. The length of the needle/instrument is determined by the following algorithm:

Calculate the vector $V = P_2 - P_1$; (F12)

Calculate the Norm of the vector V:

$$\mathrm{Norm}(V) = \sqrt{(X_2-X_1)^2+(Y_2-Y_1)^2+(Z_2-Z_1)^2};\quad\text{(F13)}$$

Calculate unit vector $V_{UNIT} = V/\mathrm{Norm}(V)$; (F14)

Find required length $L = (P(X,Y,Z)-P_1)/V_{UNIT}$. (F15)

A method other than utilizing LED'S attached to the locator and surgical instruments can be used. For example, grid/chess board references can also be used for calibration.

The combination of the system of marker coordinates together with reference points and the coordinates of the tip of a surgical instrument/needle, for example of a biopsy device, can create the virtual object of the dynamic field for surgery/needle biopsy of the tumor bed. This object combined (by appropriate SW) with the binocular AR glasses worn by for example a surgeon/breast imager creates an AR dynamic field allowing the operator full visual control of the entire ROI as defined by the marker(s).

The described method can allow the surgeon to see if the tip of his instrument(s), for example the cutting diathermy or scalpel, has 'entered' the virtual volume of tissue as defined by the markers and hence, transgressed the desired surgical margin. This transgression can also be indicated by a signal, such as for example, by a warning sound or a red (transgression) or green (non-transgression) light. By including the surgical instrument as described above in the AR scene, the surgeon is able to operate in real-time, seamlessly, without the need to periodically revert to using the locator. The surgical instrument can be seen in 3D with respect to the AR defined ROI. For example, the instrument can be seen or designated as lying anterior or posterior to the 3D wired virtual marker defined object.

In cases where tumors have responded fully or almost completely to preoperative systemic therapy, a biopsy of the suspected residual tumor bed can be done under imaging, for example with ultrasound guidance. The physician/operator can see, for example at real-time ultrasound, if the tip of the biopsy needle has 'entered' the virtual volume of tissue as defined by the markers or transgressed the desired originally defined tumor volume. This transgression can also be indicated by a signal such as for example by a warning sound or a red (transgression) or green (non-transgression) light. The biopsy needle can be seen in 3D with respect to the AR defined ROI. For example, the needle/instrument can be seen or designated as lying anterior or posterior to the 3D wired virtual marker defined object. The AR field can be image fused with the image of the imaging modality being used for the biopsy for example the ultrasound or CT or MM screen image.

The node points established by the markers and the designated reference points can be integrated with an AI program that can be combined with the above-described method to enhance the integration of the reference points and 3D virtual defined volume. AI can be used to collect data from each procedure for the establishment of a historical data set. This will allow for suggestions and alerts to surgeons, providing real time visual data for intelligent surgery.

The AR system described and the associated computer program may be used to generate a simulation model of the ROI/ROI's requiring biopsy and or excision. The markers and associated ROI/ROI'S in the simulation model can duplicate the invivo scenario and allow for teaching/review and practice of the interventional procedures prior to the actual invivo event/s.

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

It will be appreciated by persons skilled in the art that the present invention is not limited by what has been particularly shown and described herein above. Rather the scope of the invention is defined by the claims that follow.

What is claimed is:

1. An apparatus for use with at least one breast marker that is placed within breast tissue of a subject such as to designate a region of interest, the apparatus comprising:
   an augmented reality system comprising:
      augmented reality glasses;
      one or more reference markers configured to be placed on skin of the breast at respective reference points; and
      a processing unit configured to:
         determine a relationship between a position of the at least one breast marker within the breast tissue and the one or more reference markers on the skin of the breast;
         subsequently, determine locations of the at least one breast marker within the breast tissue relative the augmented reality glasses by identifying the one or more reference markers and thereby localizing the at least one breast marker within the breast tissue; and
         output augmented reality data at a location corresponding the region of interest on the augmented reality glasses.

2. The apparatus according to claim 1, wherein the one or more reference markers comprise three or more reference markers and wherein the processing unit is configured to determine the relationship between the position of the at least one breast marker within the breast tissue and the reference markers on the skin of the breast by determining respective relationships between the position of the at least one breast marker within the breast tissue and positions of each of the reference markers on the skin of the breast.

3. The apparatus according to claim 1, wherein the processing unit is configured to determine the relationship between the position of the at least one breast marker within the breast tissue and positions of each of the reference markers on the skin of the breast, by defining one or more pyramids that connect the at least one breast marker within the breast tissue and positions of the one or more reference markers on the skin of the breast.

4. The apparatus according to claim 1, wherein the one or more reference markers comprise one or more visible reference markers.

5. The apparatus according to claim 1, wherein the one or more reference markers are configured to be repositioned to new positions during a procedure that is performed on the subject's breast, and wherein the processing unit is configured to determine an updated relationship between the position of the at least one breast marker within the breast tissue and the new positions of the reference markers.

6. The apparatus according to claim 1, wherein the processing unit is configured to localize the at least one breast marker within the breast tissue by translating movement of the one or more reference markers to movement of the at least one breast marker within the breast tissue.

7. The apparatus according to claim 6, wherein the processing unit is configured to translate movement of the one or more reference markers to movement of the at least one breast marker within the breast tissue by assuming that movement of the breast tissue will not vary a distance between the at least one breast marker within the breast tissue and the one or more reference markers on the skin of the breast.

8. The apparatus according to claim 1, wherein the apparatus is for use with at least one breast marker that is placed within breast tissue of the subject prior to the procedure such as to designate a tumor volume and wherein the processing unit is configured to output augmented reality data at a location corresponding the tumor volume on the augmented reality glasses.

9. The apparatus according to claim 8, wherein the apparatus is for use a plurality of breast markers that are placed within breast tissue of the subject prior to the procedure such as to designate the tumor volume, and wherein the processing unit is configured to define pyramids that connects the plurality of breast markers within the breast tissue and positions of respective reference markers on the skin of the breast in order to define the tumor volume.

10. The apparatus according to claim 8, wherein the processing unit is configured to output an augmented reality image of the tumor volume at a location corresponding to the tumor volume on the augmented reality glasses.

11. The apparatus according to claim 8, wherein the apparatus is configured to use with a tool having a working edge and the processing unit is configured to output an augmented reality image of a real-time position of the working edge of the tool relative to the tumor volume on the augmented reality glasses.

12. An apparatus for use with at least one breast marker that is placed within breast tissue of a subject prior to a procedure such as to designate a region of interest and a locator that is configured to be placed on the breast and determine a depth of the at least one breast marker, the apparatus comprising:
  an augmented reality system comprising:
    augmented reality glasses; and
    a processing unit configured to:
      determine a relationship between a position of the at least one breast marker within the breast tissue and the locator,
      subsequently, determine a location of the at least one breast marker within the breast tissue relative the augmented reality glasses by locating the locator and thereby localizing the at least one breast marker within the breast tissue; and
      output augmented reality data at a location corresponding the region of interest on the augmented reality glasses.

13. The apparatus according to claim 12, further comprising two or more visual elements configured to be disposed on the locator, wherein the processing unit is configured to locate the locator by identifying the two or more visual elements that are disposed on the locator.

14. The apparatus according to claim 13, wherein the processing unit is configured to locate a tip of the locator based upon identifying the two or more visual elements that are disposed on the locator.

15. The apparatus according to claim 13, wherein the two or more visual elements disposed on the locator comprise two or more LEDs disposed on the locator.

16. The apparatus according to claim 13, wherein the two or more visual elements are configured to be removable from the locator.

17. The apparatus according to claim 12, wherein the processing unit is configured to localize the at least one breast marker within the breast tissue by translating movement of the locator to movement of the at least one breast marker within the breast tissue.

18. The apparatus according to claim 17, wherein the processing unit is configured to translate movement of the locator to movement of the at least one breast marker within the breast tissue by assuming that movement of the breast tissue will not vary a distance between the at least one breast marker within the breast tissue and the locator.

19. The apparatus according to claim 12, wherein the apparatus is for use with at least one breast marker that is placed within breast tissue of the subject prior to the procedure such as to designate a tumor volume and wherein the processing unit is configured to output augmented reality data at a location corresponding the tumor volume on the augmented reality glasses.

20. The apparatus according to claim 19, wherein the apparatus is for use a plurality of breast markers that are placed within breast tissue of the subject prior to the procedure such as to designate the tumor volume, and wherein the processing unit is configured to define a pyramid that connects the plurality of breast markers within the breast tissue and a position of a tip of the locator in order to define the tumor volume.

21. The apparatus according to claim 19, wherein the processing unit is configured to output an augmented reality image of the tumor volume at a location corresponding to the tumor volume on the augmented reality glasses.

22. The apparatus according to claim 19, wherein the apparatus is configured to use with a tool having a working edge and the processing unit is configured to output an augmented reality image of a real-time position of the working edge of the tool relative to the tumor volume on the augmented reality glasses.

* * * * *